(12) United States Patent
Broqua

(10) Patent No.: US 6,521,644 B1
(45) Date of Patent: Feb. 18, 2003

(54) COMPOSITIONS FOR PROMOTING GROWTH

(75) Inventor: Pierre Broqua, Thoiry (FR)

(73) Assignee: Ferring BV, Hoofddorp (NL)

( * ) Notice: Subject to any disclaimer, the term of this patent is extended or adjusted under 35 U.S.C. 154(b) by 0 days.

(21) Appl. No.: 09/937,031

(22) PCT Filed: Mar. 21, 2000

(86) PCT No.: PCT/IB00/00393

§ 371 (c)(1), (2), (4) Date: Jan. 7, 2000

(87) PCT Pub. No.: WO98/19998

PCT Pub. Date: May 14, 1998

(30) Foreign Application Priority Data

Mar. 23, 1999 (GB) .............................. 9906715

(51) Int. Cl.$^7$ ......................... A61K 31/44; A61K 31/41; A61K 31/40
(52) U.S. Cl. ......................... 514/343; 514/359; 514/423
(58) Field of Search ................ 514/343, 359, 514/423

(56) References Cited

FOREIGN PATENT DOCUMENTS

| WO | 91/16339 | 10/1991 |
|---|---|---|
| WO | 93/08259 | 4/1993 |
| WO | 95/15309 | 6/1995 |
| WO | 98/19998 | 5/1998 |
| WO | 98/25644 | 6/1998 |

OTHER PUBLICATIONS

Kiyohara et al. "Cytoprotective effects of epidermal growth factor (EFG) ointment cantaining nafamostat, a protease inhibitor, on tissue damage at burn sites in rats," *Biol. Pharm. Bull.*, 1993, pp. 1146–1149, vol. 16, No. 11.

Martin et al., "Dipeptidyl peptidase IV (DPP–IV) from pig kidney cleaves analogs of bovine growth hormone–releasing factor (bGRF) modified at position 2 with Ser, Thr or Val. Extended DPP–IV substrate specificity," *Biochemica et Biophysica Acta.*, Aug. 7, 1993, pp. 252–260, vol. 1164, No. 3, (Abstract only).

R. Mentlein et al., "Dipeptidyl–peptidase IV (CD26)–role in the inactivation of regulatory peptides," *Reglutory Peptides* 85, pp. 9–24, Elsevier Science BV, 1999.

D. Ashworth et al., "2–Cyanopyrrolidides as potent, stable inhibitors of dipeptidyl peptidase IV," *Bioorganic & Medicinal Chemistry Letters*, vol. 6 No. 10, pp. 1163–1166, Elsevier Science Ltd, 1996.

J. Bongers et al., "Kinetics of dipeptidyl peptidase IV proteolysis of growth hormone–relating factor and analogs," *Biochim Biophys Acta,*. Elsevier Science Publishers BV, 1992.

R. Campbell et al., "Enhanced stability and potency of novel growth hormone–releasing factor (GRF) analogues deerived from rodent and human GRF sequences", *Peptides*, vol 15 No. 3, pp. 489–495, Pergamon, 1994.

M. Prager et al., "Dipeptidyl peptidase IV and aminopeptidase in burn wound exudates: implications for wound healing," *The Journal of Trauma*, vol 36 No. 5, pp. 629–633, Williams & Wilkins, 1994.

R. Mentlien et al., "Dipeptidyl–peptidase IV hydrolyses gastric inhibitory polypeptide, glucagon–like peptide–1)7–36)amide, peptide histidine methionine and is responsible for their degradation in human serum," *Eur. J. Biochem.*, pp. 829–835, FEBS, 1993.

Reynolds, "Martindale the extra pharmacopeia," *Royal Pharmaceutical Society*, pp. 1271, 1272, 1283, 1284, and 1293, London, 1996.

Primary Examiner—Raymond Henley, III
(74) *Attorney, Agent, or Firm*—Foley & Lardner

(57) ABSTRACT

Inhibitors of dipeptidyl peptidase IV and pharmaceutical compositions comprising these inhibitors are useful in the treatment of short stature due to Growth-Hormone deficiency and for promoting GH-dependent tissue growth or regrowth.

16 Claims, No Drawings

COMPOSITIONS FOR PROMOTING GROWTH

This is a 371 of PCT/IB00/00393 filed Mar. 21, 2000.

The present invention relates to agents and compositions for promoting animal growth, e.g. in underdeveloped humans, and for accelerating tissue repair and regeneration.

Inhibitors of DP-IV

Dipeptidyl peptidase IV (DP-IV, also dipeptidyl aminopeptidase IV, DPP-IV, DAP-IV, EC 3.4.14.5) is a serine peptidase that cleaves the amino-terminal dipeptide from peptides and proteins. It recognises substrates wherein the N-terminal sequence is X-Pro or X-Ala. Inhibitors of DP-IV have been proposed as therapeutic agents for the treatment of inflammatory diseases and AIDS. Generally, the known inhibitors of DP-IV are analogues of the substrate. Examples of DP-IV inhibitors are those disclosed in DD 296 075 A5 (Neubert et al., November 1991), WO91/16339 (Bachovchin et al., October 1991), WO93/08259 (Bachovchin et al, April 1993), WO95/15309 (Jenkins et al., June 1995), WO98/19998 (Villhauer, May 1998), WO99/46272 (Scharpe et al., September 1999) and WO99/61431 (Demuth et al, December 1999). Prodrugs of some of these inhibitors have also been described in WO99/67278 and WO99/67279 (both Demuth et al, December 1999).

The following table sets out general types of DP-IV inhibitor compounds, and specific examples thereof which are amongst those preferred for use in the present invention; it also indicates the patent publications from whose broader range of disclosed compounds these types and examples are drawn. It is emphasised that all DP-IV inhibitors disclosed in the quoted DO and WO specifications can be used in the present invention, and reference is positively directed to these prior specifications for full information on the general and more specific formulae and individual compounds concerned. For example, in the table below the indicated pyrrolidine and thiazolidine rings can be replaced by a wide range of other heterocycles of various ring sizes and/or the indicated aminoacyl moieties can be replaced by a wide range of others, as taught by the indicated publications, to give other DP-IV inhibitors for use in the present invention.

Amino-acyl pyrrolididies and thiazolidides (see DD 296 075 A5), e.g.

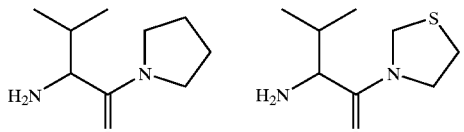

Amino-acyl pyrrolidine aldehydes (see DD 296 075 A5 and WO95/15309), e.g.

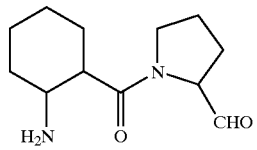

Amino-acyl pyrrolidine boronic acids (see WO91/16339 and WO93/08259), e.g.

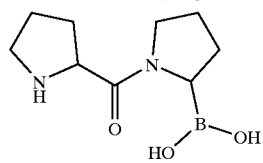

Amino-acyl pyrrolidine nitriles (see WO95/15309 and WO98/19998), e.g.

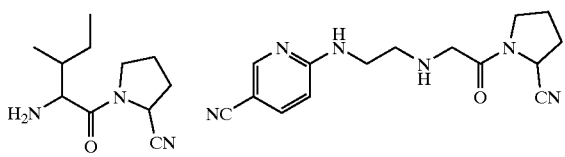

Actions of Growth Hormone

Growth Hormone (GH, Somatotropin) is secreted by the pituitary in response to a hypothalamic signal in the form of Growth Hormone Releasing Hormone (GHRH). The most abundant isoform of human GH is a 191-residue peptide and GHRH is a 44-residue peptide. GH is a key factor in promoting the normal development of children, and GH deficiency can lead to dwarfism. In adults the importance of GH is less well defined, although plasma levels of GH are similar in adults and children. It is possible that GH plays a role in tissue repair following injury.

The current therapeutic options for GH deficiency include the administration of synthetic GH or of GHRH. However, since both these hormones are peptidic, it is not possible to give them orally. Administration is usually by injection, which can be distressing for the patient (and particularly for children) despite the development of needleless injection systems.

Furthermore, a single injection of GHRH is only an approximation of the pulsatile release of this factor from the hypothalamus. Finally, because both are relatively large peptides, both GHRH and particularly GH are expensive to produce. In consequence, there exists an unmet need for a therapeutic agent that will promote the actions of GH. We have now found that DP-IV inhibitors can increase the concentration of circulating GH.

A first aspect of the present invention is a pharmaceutical composition for the treatment of dwarfism and sub-normal growth (e.g. in children), and for promoting tissue repair (e.g. following injury), which composition is characterized by the inclusion of inhibitor of DP-IV. A second aspect of the present invention is a novel use of inhibitors of DP-IV, namely in the treatment of dwarfism and tissue injury. A third aspect of the invention is an improved protocol for accelerating the growth of children and the regeneration of injured tissue, wherein the subject is administered a composition comprising DP-IV inhibitor.

The use of DP-IV inhibitors in this way presents many advantages over current treatment regimens that involve GH or GHRH. GHRH and particularly GH are large peptides that are either isolated from natural sources (such as animal brain preparations) or prepared in culture using recombinant cells. Isolation from animal sources requires that attention be paid to risk of disease transmission and the presence of antigenic protein contaminants. Recombinant hormones are less likely to transmit human pathogens but are still potentially contaminated with antigenic protein. GHRH can be prepared synthetically, but such a synthesis is expensive and necessitates careful purification of the product. In contrast, DP-IV inhibitors are small molecules that are readily accessible using standard synthetic methods. They are non-antigenic, easy to purify and inexpensive.

A further advantage is that DP-IV inhibitors are in many cases biologically active after oral administration. This is in contrast to GH and GHRH, which must be administered by injection. Hence the use of DP-IV inhibitors leads to a less invasive protocol that is less stressful for the patient.

In a first aspect, the present invention provides a pharmaceutical composition for the treatment of sub-normal development or dwarfism. The composition is particularly effective for the treatment of sub-normal development or dwarfism due to growth hormone deficiency. The invention equally provides a composition for the promotion of tissue regeneration.

These compositions are characterized in that they comprise inhibitor of DP-IV. The compositions may further include such pharmaceutically acceptable excipients as are generally known in the art, such as diluents, carriers, bulking agents, binding agents, dispersants, stabilizers and the like.

In the context of the present invention, a compound is considered to be an inhibitor of DP-IV if it inhibits the action of the enzyme at a concentration of 1 μM. Preferably, such a compound inhibits the action of DP-IV at concentrations below 100 nM and does not inhibit other enzymes at concentrations below 1 μM. The following table sets out general types of DP-IV inhibitor compounds, and specific examples thereof which are amongst those preferred for use in the present invention; it also indicates the patent publications from whose broader range of disclosed compounds these types and examples are drawn. It is emphasised that all DP-IV inhibitors disclosed in the quoted DD and WO specifications can be used in the present invention, and reference is positively directed to these prior specifications for full information on the general and more specific formulae and individual compounds concerned. For example, in the table below the indicated pyrrolidine and thiazolidine rings can be replaced by a wide range of other heterocycles of various ring sizes and/or the indicated aminoacyl moieties can be replaced by a wide range of others, as taught by the indicated publications, to give other DP-IV inhibitors for use in the present invention.

Amino-acyl pyrrolididies and thiazolidides (see DD 296 075 A5), e.g.

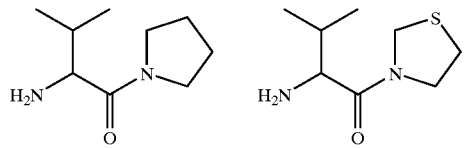

Amino-acyl pyrrolidine aldehydes (see DD 296 075 A5 and WO95/15309), e.g.

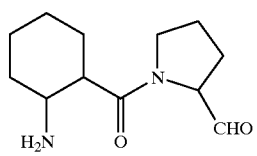

Amino-acyl pyrrolidine boronic acids (see WO91/16339 and WO93/08259), e.g.

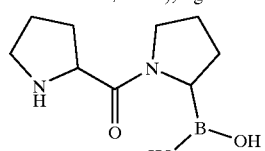

Amino-acyl pyrrolidine nitriles (see WO95/15309 and WO98/19998), e.g.

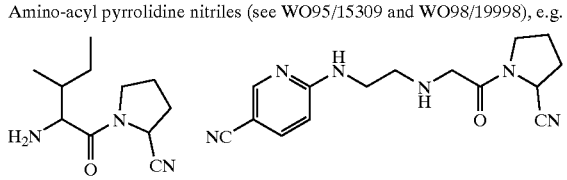

In a preferred embodiment of the invention, the inhibitor of DP-IV is an amino-acylpyrrolidine nitrile. Particularly preferred are those amino-acyl pyrrolidine nitrites disclosed in WO95/15309 and WO98/19998.

The compositions according to the present invention may be formulated for administration to human subjects by any of the known routes, including oral administration, transmucosal administration (such as buccal, sublingual, intranasal, vaginal and rectal administration), transdermal administration or injection (including intravenous, intramuscular and subcutaneous injection). A preferred route of administration is oral administration. In this case the composition is suitably formulated as a tablet or capsule.

In a second aspect, the present invention comprises a new use for compounds that are known to be inhibitors of DP-IV, which is as therapeutic agents for the treatment of subnormal development and dwarfism or for the promotion of tissue regeneration.

In a third aspect, the present invention comprises an improved method for the treatment of sub-normal development and dwarfism, particularly that due to growth hormone deficiency, and for the promotion of tissue regeneration, wherein the patient is administered a pharmaceutical composition comprising a therapeutically effective amount of inhibitor of DP-IV. The treatment may involve the use of said composition alone or in conjunction with other agents such as have been described heretofore. The administration may be as a single dose or as divided doses taken at intervals of, for example, 2–6 hours. In a particularly preferred dosing schedule, the composition is given once per day in the evening prior to sleep. The course of treatment might last for a period of a few days or weeks when used to promote tissue regeneration, or for a longer period when used to treat sub-normal development. The responsible physician will determine when a suitable clinical endpoint has been reached, as well as the details of the dosing regimen.

EXAMPLES

Example 1

Preparation of Inhibitors

The inhibitors of DP-IV can be prepared following the methods outlined on the literature. The synthesis of aminoacyl pyrrolidine nitrites is described in WO95/15309 and WO98/19998. The following method is illustrative of these methods.

Example 1A

Synthesis of (2S)-N-isoleucylpyrrolidine-2-carbonitrile

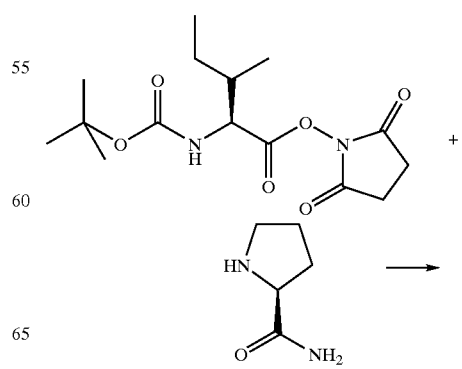

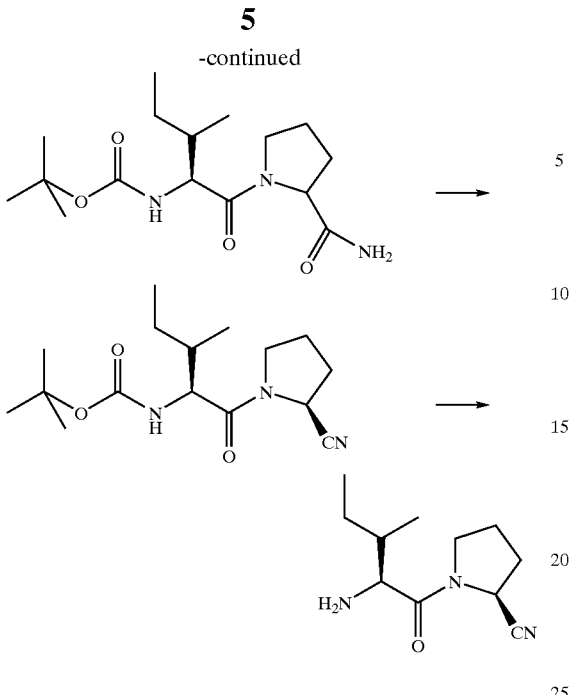

(a) tert-Butyloxycarbonyl-isoleucylprolinamide

To a stirred suspension of prolinamide hydrochloride (225 mg, 1.50 mmol) in dry dichloromethane (15 mL) was added diisopropylethylamine to give a clear basic (pH 9) solution. N-(tert-Butyloxycarbonyl-isoleucyloxy)succinimide (328 mg, 1.0 mmol) was added in one portion and the mixture was stirred at room temperature for 16 hours under a nitrogen atmosphere. The solvent was evaporated in vacuo and the residue was partitioned between ethyl acetate and 0.3N potassium hydrogensulphate solution. The organic layer was washed with saturated sodium hydrogencarbonate solution, water and brine, dried over sodium sulphate, and concentrated in vacuo. The residue was purified by filtration through a short plug of silica gel, eluting with hexane/ethyl acetate (10:90) then ethyl acetate. Concentration of the product-containing eluate gave the title compound as a colourless foaming glass; 301 mg (92%).

$^1$H NMR (CDCl$_3$): δ 6.90 (1H, br. s); 5.51 (1H, br. s); 5.18 (1H, d, J=9.6 Hz); 4.62 (1H, dd, J=2.6 & 7.0 Hz); 4.29 (1H, dd, J=8.4 & 9.2 Hz); 3.79–3.58 (2H, m); 2.36 (1H, m); 2.09–1.57 (5H, m); 1.43 (9H, s); 1.17 (1H, m); 0.95 (3H, d, J=6.6 Hz); 0.90 (3H, t, J=7.3 Hz) ppm.

(b) (2S)-N-(tert-Butyloxycarbonyl-isoleucyl)pyrrolidine-2-carbonitrile

To a stirred solution of the amide of part (a) (203 mg, 0.62 mmol) in dry pyridine (10 mL) under a nitrogen atmosphere was added imidazole (84 mg, 1.24 mmol). The mixture was cooled to −35° C. and then phosphorus oxychloride (0.25 mL, 2.48 mmol) was added dropwise. The mixture was stirred for 1 hour, during which time the temperature was allowed to rise to −20° C., and the solvent was evaporated in vacuo. The residue was purified by chromatography on silica gel to give the title compound as a colourless oil; yield 180 mg (94%).

$^1$H NMR (CDCl$_3$): δ 5.14 (1H, d, J=9.2 Hz); 4.80 (1H, dd, J=2.6 & 7.1 Hz); 4.22 (1H, dd, J=7.9 & 9.1 Hz); 3.81 (1H, m); 3.71 (1H, m); 2.30–2.12 (4H, m); 1.75 (1H, m); 1.60 (1H, m); 1.42 (9H, s); 1.19 (1H, m); 0.97 (3H, d, J=6.9 Hz); 0.91 (3H, t, J=7.3 Hz) ppm.

$^{13}$C NMR (CDCl$_3$): δ 171.7; 155.6; 118.0; 79.6; 56.0; 46.5; 46.0; 37.8; 29.6; 28.1; 25.0; 24.2; 15.2; 10.9 ppm.

(c) (2S)-N-(isoleucyl)-pyrrolidine-2-carbonitrile trifluoroacetate

The nitrile of part (b) was dissolved in trifluoroacetic acid and the solution was stirred at room temperature for 1 hour. The solvent was evaporated in vacuo and the residue was dissolved in water. The solution was lyophilised to give the title compound as a white fluffy solid; yield 60 mg.

FAB Mass Spec.: Calculated m/e 209.3; Found 210.2 (M+H)$^+$ $^1$H NMR (D$_2$O): δ 4.3 (1H, m); 3.64 (1H, d, J=5.6 Hz); 3.16 (2H, m); 1.86–1.48 (5H, m,); 0.98 (1H, m); 0.68 (1H, m); 0.51 (3H, d, J=6.9 Hz); 0.38 (3H, t, J=7.3 Hz) ppm.

$^{13}$C NMR (D$_2$O): δ 169.7; 119.7; 57.3; 48.6; 48.1; 36.9; 30.2; 25.8; 24.5; 15.4; 11.5 ppm.

Example 1B

Synthesis of (2S)-N-((2'S)-2'-amino-3',3'-dimethylbutanoyl)pyrrolidine-2-carbonitrile.

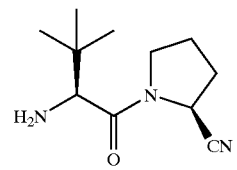

This was prepared following the method of Example 1A by replacing the isoleucine derivative with the corresponding tert-butylglycine derivative.

$^1$H NMR (CD$_3$OD): δ 4.86–4.81 (1H, m); 4.04 (1H, s); 3.77–3.71 (2H, m); 3.34 (2H, s); 2.34–2.08 (4H, m); 1.14 (9H, s) ppm.

$^{13}$C NMR (CD$_3$OD): δ 167.40, 117.99, 58.78, 46.53, 34.21, 29.54, 25.22, 25.03 ppm.

Example 2

Effect on Circulating Growth Hormone

Animals

Experiments were conducted in male Sprague-Dawley rats (200–220 g) obtained from Iffa Credo (L'Arbresle, France), fed with standard laboratory chow ad libitum and kept on a 12 h light-dark in a temperature- and humidity-controlled room.

Surgery

Rats were weighed and anesthetized with Narcorene. The ventral side of the throat was shaved and an incision was made down the center of the throat. The right jugular vein was exposed and cannulated using a polythene tubing (OD 1.0 mm) connected to a medical grade silicone tubing (OD 0.94 mm) (silicone side in the jugular vein). The tubing was secured and the polythene side was externalized through an incision made on the dorsal side of the neck. The catheter was rinsed with 300 μL of a Ringer solution containing 0.1% heparin. Rats were allowed to recover for at least 24 hours in individual cages with food and water available ad libitum.

Experimental Procedure

The compound of Example 1B (3 mg/kg, i.v.) or its vehicle was injected 15 minutes before an injection of GHRH (0.1 μg/kg, i.v.). Blood samples (200–250 μL) were removed immediately before inhibitor and GHRH injections, and then 5, 10, 15, 20, 30 and 60 min post-GHRH. Each blood sample was replaced with an equivalent volume of a Ringer solution containing 0.1% heparin.

Plasma was extracted and stored at −20° C. until determinations of GH by RIA.

Results

The compound of Example 1B potentiated the GH surge induced by the administration of GHRH (Table 1). Integrated GH responses were 720.2±217.0 ng/ml.60 min and 5072.8±837.3 ng/ml.60 min in the vehicle- and inhibitor-treated group respectively (p<0.05).

TABLE 1

Effects of the DP-IV inhibitor of Example 1B on the GH surge induced by an intravenous injection of GHRH. Results are mean GH ng/ml of 6 rats ± s.e.m.

| | Time (min) | | | | | | | | |
|---|---|---|---|---|---|---|---|---|---|
| | −15 | 0 | 5 | 10 | 15 | 20 | 30 | 60 | AUC |
| GHRH | 42.1 ± 12.5 | 40.1 ± 8.0 | 155.7 ± 25.1 | 91.0 ± 15.6 | 61.0 ± 12.9 | 53.6 ± 12.5 | 34.1 ± 8.2 | 26.7 ± 3.0 | 720.2 ± 217.0 |
| GHRH + Inhibitor | 50.5 ± 16.4 | 33.4 ± 6.9 | 483.0 ± 91.0 | 309.5 ± 55.40 | 164.3 ± 28.3 | 103.1 ± 18.1 | 52.1 ± 7.7 | 26.3 ± 3.3 | 5072.8 ± 837.3 |

The results obtained indicate that inhibitors of DP-IV are able to increase circulating levels of growth hormone and hence are useful in the treatment of sub-normal development due to growth hormone deficiency and other conditions where the promotion of tissue growth is important.

Example 3

Pharmaceutical Formulation
3A—50 mg Tablet
Tablets containing the equivalent of 50 mg of the compound of Example 1A as the active agent are prepared from the following:

| | |
|---|---|
| Compound of Example 1A (as trifluoroacetate salt) | 154.5 g |
| Corn starch | 53.5 g |
| Hydroxypropylcellulose | 13.5 g |
| Carboxymethylcellulose calcium | 11.0 g |
| Magnesium stearate | 2.0 g |
| Lactose | 165.5 g |
| Total | 400.0 g |

The materials are blended and then pressed to give 2000 tablets of 200 mg, each containing the equivalent of 50 mg of the free base of the compound of Example 1A.

3B—100 mg Vaginal suppository
Suppositories suitable for vaginal administration and containing the equivalent of 100 mg of the compound of Example 1A as the active agent are prepared from the following:

| | |
|---|---|
| Compound of Example 1A (as trifluoroacetate salt) | 154.5 g |
| Corn starch | 210.0 g |
| Colloidal silica | 2.5 g |
| Povidone 30 | 49.0 g |
| Magnesium stearate | 23.0 g |
| Adipic acid | 57.0 g |
| Sodium bicarbonate | 43.0 g |
| Sodium lauryl sulphate | 5.0 g |
| Lactose | 456.0 g |
| Total | 1000.0 g |

The materials are blended and then pressed to give 1000 suppositories of 1 g, each containing the equivalent of 100 mg of the free base of the compound of Example 1A.

The foregoing Examples are illustrative of the invention as disclosed herein, but are not intended to be limiting. Such extensions as would be considered equivalent by one skilled in the art are included within the scope of the invention and the Claims that further define that scope.

One or more DP-IV inhibitors may be used as the sole component active for the specified purposes of the composition and method of the invention.

What is claimed is:

1. A method for the treatment of sub-normal development or dwarfism, comprising administering to a patient in need thereof a pharmaceutical composition comprising an inhibitor of dipeptidyl peptidase IV.

2. The method of claim 1, wherein the sub-normal growth or dwarfism is due to growth hormone deficiency.

3. The method of claim 1, wherein the inhibitor of dipeptidyl peptidase IV comprises amino-acyl pyrrolidine nitrile.

4. The method of claim 1, wherein the pharmaceutical composition is formulated for oral administration.

5. The method of claim 4, wherein the pharmaceutical composition is formulated as a tablet or capsule.

6. The method of claim 1, wherein the pharmaceutical composition is administered once per day in the evening.

7. A method of tissue regeneration following an injury, comprising administering to a patient in need thereof a pharmaceutical composition comprising an inhibitor of dipeptidyl peptidase IV.

8. The method of claim 7, wherein the inhibitor of dipeptidyl peptidase IV comprises amino-acyl pyrrolidine nitrile.

9. The method of claim 7, wherein the pharmaceutical composition is formulated for oral administration.

10. The method of claim 9, wherein the pharmaceutical composition is formulated as a tablet or capsule.

11. The method of claim 7, wherein the pharmaceutical composition is administered once per day in the evening.

12. A method of tissue regeneration, comprising administering to a patient in need thereof a pharmaceutical composition comprising an inhibitor of dipeptidyl peptidase IV, wherein the inhibitor of dipeptidyl peptidase IV is the sole active component of the pharmaceutical composition which has tissue regenerative effect.

13. The method of claim 12, wherein the inhibitor of dipeptidyl peptidase IV comprises amino-acyl pyrrolidine nitrile.

14. The method of claim 12, wherein the pharmaceutical composition is formulated for oral administration.

15. The method of claim 14, wherein the pharmaceutical composition is formulated as a tablet or capsule.

16. The method of claim 12, wherein the pharmaceutical composition is administered once per day in the evening.

* * * * *